United States Patent [19]

Pegg et al.

[11] Patent Number: 5,663,318
[45] Date of Patent: *Sep. 2, 1997

[54] ASSAY PREPARATION CONTAINING CAPTURE AND DETECTION POLYNUCLEOTIDES COVALENTLY BOUND TO SUBSTRATES WITH A HETEROBIFUNCTIONAL CROSSLINKING AGENT

[76] Inventors: Randall Kevin Pegg, 5085 First Coast Hwy., Amelia Island, Fla. 32034; Mary Starnes Saunders, Rte. 3 Box 106-1, Monticello, Fla. 32344

[*] Notice: The term of this patent shall not extend beyond the expiration date of Pat. No. 5,279,955 and 5,436,147.

[21] Appl. No.: 381,231

[22] Filed: Jan. 31, 1995

Related U.S. Application Data

[63] Continuation-in-part of Ser. No. 78,753, Jun. 16, 1993, Pat. No. 5,436,147, and a continuation-in-part of Ser. No. 663,120, Mar. 1, 1991, Pat. No. 5,279,955.

[51] Int. Cl.$^6$ .................. C07H 21/04; C12N 11/06; G01N 33/549; C12Q 1/68
[52] U.S. Cl. .................. 536/24.3; 435/6; 435/174; 435/181; 436/532; 530/816
[58] Field of Search ............... 435/6, 7, 92, 181, 435/174; 536/24.3; 530/816; 436/532

[56] References Cited

U.S. PATENT DOCUMENTS

| | | | |
|---|---|---|---|
| 4,657,873 | 4/1987 | Gadow et al. | 436/532 |
| 4,808,530 | 2/1989 | Means et al. | 435/180 |
| 5,002,883 | 3/1991 | Bieniarz et al. | 435/176 |
| 5,200,313 | 4/1993 | Carrico | 435/6 |
| 5,200,314 | 4/1993 | Urdea | 435/6 |
| 5,273,882 | 12/1993 | Snitman et al. | 435/6 |
| 5,279,955 | 1/1994 | Pegg | 435/181 |
| 5,312,728 | 5/1994 | Lizardi et al. | 435/6 |
| 5,328,825 | 7/1994 | Warren, III et al. | 435/6 |
| 5,436,147 | 7/1995 | Pegg et al. | 435/181 |

*Primary Examiner*—David M. Naff

[57] ABSTRACT

Heterofunctional crosslinking agents are used to produce a device for detecting a target polynucleotide. Synthetic single stranded capture and detector polynucleotides are covalently immobilized to plastic surfaces by novel heterofunctional reagents. The capture and detector polynucleotides are covalently attached through a synthetic region of amine-bearing nucleotides that interact with reactive moieties on the heterofunctional crosslinker. The regions of the capture and detector polynucleotides that can hybridize a diagnostically important target polynucleotide are protected from binding to a solid phase support by intrastrand pairing. This system provides monolayers of immobilized polynucleotides with precise orientation and unimpaired diagnostic coding regions.

7 Claims, 4 Drawing Sheets

ASSAY PREPARATION CONTAINING CAPTURE AND DETECTION POLYNUCLEOTIDES COVALENTLY BOUND TO SUBSTRATES WITH A HETEROBIFUNCTIONAL CROSSLINKING AGENT

This application is a continuation-in-part of application Ser. No. 08/078,753, filed Jun. 16, 1993, now U.S. Pat. No. 5,436,147, and a continuation-in-part of application Ser. No. 07/663,120, filed Mar. 1, 1991, now U.S. Pat. No. 5,279,955.

BACKGROUND OF THE INVENTION

1. Field of the Invention

This invention utilizes novel heterobifunctional compositions to immobilize polynucleic acids on plastic surfaces. More specifically this invention comprises molecules with hydrophobic regions that can intercalate into plastic and hydrophilic reactive groups that can covalently attach to specific loci on a nucleic acid polymer. Further, these novel nucleic acid surfaces result in new assay technologies.

2. Background Information

The practice of biotechnology, and particularly diagnostics, has increased the demand for products requiring reagent immobilization on substrates. "Reagents" includes proteins, nucleic acids, cells, drugs, and small molecule haptens. Substrates are insoluble matrices for immobilization and can be plastic, glass, silica, carbon, cellulose, or other materials. Plastics are particularly useful substrates as they can be formed into a variety of shapes such as cups, discs, dipsticks, spheres, fibers, tubes, membranes, and particles. Plastics are also used as surface coatings that can be modified further. Additionally, plastics have a high degree of biocompatability, and may be produced of materials having excellent optical properties. Typical plastics useful as substrates include polypropylene, polystyrene, polyethylene, polyvinyl chloride, polysulfone, polycarbonate, cellulose acetate and others. Plastics of styrene, vinyl chloride, acrylic and carbonate are widely used when optical properties are a consideration.

Plastics are often used directly as substrates for immobilization of macromolecules. Polystyrene and polyvinyl chloride will anchor large molecules by electrostatic attraction. However, small molecules require attachment to larger "carrier" molecules before being bound to the plastic. Also, poor direct binding to most plastics limits the use of adsorption immobilization to high surface area systems. For instance, polystyrene latex particles can immobilize far more protein molecules per gram of plastic than molded polystyrene products.

Modification of the plastic surface has been used to increase thee electrostatic interaction and increase the binding of some reagents. Electrostatic interactions alone will immobilize only a limited number of reagents. Detergents introduced in the system can cause reagent loss.

Reagent molecules are typically mobilized on a substrate by way of a linker molecule. Homobifuctional and heterobifunctional compounds have been devised to link a group present on the reagent to a group present on the substrate. As examples, disuccimidyl suberate and glutaraldehyde are homobifunctional compounds that can covalently bridge an amine group on a reagent molecule to an amine group present on a substrate, such as aminopolystyrene. Additionally, some plastics, such as methyl methacrylate and polyethylvinylacetate, have been developed to bear hydroxyls that can be convened to reactive intermediates. Reactive groups that can be provided include epoxides, hydroxysuccinimide esters, aldehydes, nitrophenyl chloroformate, activated thiols, trityl, tresyl chloride, or other means for reacting free amines, hydroxides or sulfhydryls.

Reagents can be specific nucleic acid sequences. Both DNA and RNA surface coatings can be used to develop novel diagnostic technologies.

Diagnostic tests using nucleic acid sequences have become popular over the past decade since genetic sequence information usually occurs with greater species uniqueness than does protein antigens or isozymes. Diagnostic nucleic acids may be DNA or RNA. Usually the tests employ sample "target" nucleic acids bound to a membrane through ionic and hydrophobic interaction and "probed" by hybridizing a known nucleic acid sequence that has been labeled in some manner. Hybridization of nucleic acid polymers is sequence specific, only two very closely related single nucleic acid chains will form interstrand double strand polymers. When hybridizing nucleic acid polymers the target and probe strands must first be heated to a melting temperature prior to sequence specific annealing. The melting/reannealing temperatures are dependent on the base sequence and length of the strand. In general, short adenine/thymine rich sequences melt more readily than longer strands incorporating guanine/cytosine rich regions. Further, RNA generally melts at temperatures lower than a DNA strand of similar length and base composition.

It is an essential feature of nucleic acid absorption to substrates that the strands must be denatured to efficiently immobilize. Accordingly, mobilization often interferes with the ability of a nucleic acid sequence to hybridize in an assay. DNA is commonly immobilized by absorption to nitrocellulose, nylon, or hyrdoxyapatite. In order for the DNA to remain insolubilized throughout the assay the strand must be of sufficient length to form several attachment points, this form of absorption often slows the ability of immobilized target DNA to efficiently reanneal with labeled probe DNA. Low molecular weight oligonucleotides and RNA are usually immobilized through a process of absorption and covalent attachment to nylon membranes. For covalent attachment to occur amines on the target sequence must be crosslinked to amines on the support. For single strand DNA, RNA and oligonucleotides the free amines of adenine, guanine, and cytosine are often utilized, rendering these bases unavailable for use in forming interstrand diagnostic interactions with labeled probe. Several previous attempts have utilized artificial nucleotides that have free amine groups available for crosslinking. These molecules must be added to the probe strand prior to linking to the amine on the support. One example employs synthetic nucleotide triphosphates with aminoalkyl function groups extending from the base, added to the 5' end of a DNA chain using polynucleotide kinase. This form of an attachment has some use for double strand DNA where amine bearing residues are blocked by interstrand hydrogen bonds, but offers little advantage for single strand DNA and RNA. Covalent crosslinking of polynucleotides to nylon membranes is also accomplished by generation of photoadducts. This process involves the separate steps of absorbing DNA or RNA to a nylon membrane, drying the membrane and using ultraviolet light (usually 254 nm wavelength) to nonspecifically attach bases to the free amines of the nylon. Covalent attachment of nucleotides often renders the DNA useless for diagnostic purposes. For example, crosslinking of amines and carboxylic acids using carbodiimide methods that work well for proteins will render nucleic acids insoluble through interstrand covalent bonds. Aldehydes, such as glutaraldehdye, can attach to hydroxyl groups throughout the length of the polymer's sugar backbone rather than at specific loci, and may crosslink strands together preventing annealing with a labeled probe sequence.

The nonspecific nature of attachment presents difficulties in performing the assay. Probe DNA can bind nonspecifically to the support. To reduce nonspecific "background" binding the hybridization solution must contain a variety of additives, including random lengths of DNA from sources foreign to the target sequences, as well as albumin and polyalcohols. These complex solutions are often sources for error in the diagnostic laboratory, placing severe constraints on the interpretation of data.

The ideal method of nucleic acid immobilization would involve loci specific crosslinking to a support. The loci would be in a portion of the strand that does not participate in hybridization reactions. Further, the ideal support would be a plastic material that is nonporous and has a low surface area to minimize nonspecific interactions with a probe.

Modifications of the plastic surfaces to bear amines, hydroxyls, and sulfhydryls that can be crosslinked or otherwise modified, often results in undesirable characteristics, particularly opacity or decreased structural integrity.

One system that has become available involves incorporation of a methyl imine function. This product requires the end user to convert the methyl imine functionality to a reactive group by addition of crosslinkers (NUNC, Naperville, Ill.). Another system treats plastic with a copolymer of phenylalanine and lysine amino acids to provide a support for a crosslinker (U.S. Pat. No. 4,657,873; Gadow, et al.). Gadow et al. is typical of the other prior attempts at forming reactive surfaces in which reagent immobilization requires several steps and usually entails crosslinking a nucleophile on the reagent molecule with a nucleophile on the plate.

Bienarz et al. (U.S. Pat. No. 5,002,883) also uses an amine bearing surface in combination with a "bridging" molecule to crosslink a reagent molecule to a plastic surface. As does Tetsuo et al. (UK Patent number GB2184127A) which specifically requires hydrophilic functional groups on the surface prior to forming a bond between the reagent and the surface. Packard et al. (U.S. Pat. No. 4,889,916) has a similar requirement for two functional groups to be crosslinked, however, in the case of Packard the reaction is between sulfhydryl groups on both the substrate and the reagent molecule.

The technology of Means et al. (U.S. Pat. No. 4,808,530) produces reagent bearing surfaces by converting hydrophilic groups on proteins to hydrophobic moieties. When the derivatized proteins are contacted to unmodified plastics, the protein is bound by nonspecific adsorption to the surface.

All of the above technologies require a plurality of steps to modify the surface and then crosslink the reagent molecule of interest, or as in the case of Means et al., to modify the protein itself for attachment. Bieniarz et al. describe their derivatization process as requiring several steps over several hours. Typical procedures involve a one hour pretreatment of a prederivatized aminopolystyrene bead, followed by one hour derivatization with several clean up steps; the final step of adding reagent member required overnight incubation. Likewise, Gadow et al. describes a first derivatization step involving heating and mixing, followed by agitation for 30 minutes at room temperature, followed by a 24 hour incubation. At this stage the technology still is incapable of protein binding. The treated plastic resin must be activated for an additional 30 minutes with glutaraldehyde, the actual crosslinking reagent, and washed prior to protein binding.

Means et al. stipulates protein modification prior to binding to a surface. The proteins were modified and purified over the course of several hours, and plastic surfaces were contacted with the protein for an additional several hours. Packard et al. describes labeling of protein species using a heterobifunctional crosslinker. As in Means et al., the Packard technology involves several steps to modify a protein surface, again requiring several hours and extensive purification.

Tetsuo et al. specifies modifying both the protein and the plastic surface. Introduction of thiol groups into proteins required 1 hour plus gel filtration cleanup. Activation of a plastic support required several sequential steps over several hours, plus removal of the reactants. Immobilization of derivatized protein required an additional 24 hours plus cleanup.

The art of polynucleotide identification by sequence specific hybridization assay is well known. U.S. Pat. No. 4,358,535 to Falkow et al. discloses the use of labeled probes in diagnostic reactions. Previous attempts at overcoming the barriers to nucleic acid target sequence immobilization have utilized noncovalent means. Typical of these attempts are Urdea, U.S. Pat. No. 5,200,314. This invention relies on a plurality of steps to isolate a specific target sequence. The technique hybridizes a biotinylated probe to a complementary target sequence, then purifies the target sequence using avidin attached to a column to bind the biotin of the complex. The method leads to a sequence that could be amplified in vitro after desorbing the target nucleotide from the avidin/biotin/capture sequence. Separate technology and apparatus were required for analysis. Some past attempts have utilized specific antibody to DNA, RNA or combinations thereof. Typical of these systems are U.S. Pat. No. 5,200,313 to Carrico using anti-hybrid antibodies, and U.S. Pat. No. 5,273,882 to Snitman employing a complexing agent attached to a nucleic acid probe. Some workers have immobilized oligonucleotides to insoluble substrates using modified copolymers (Sutton et al., U.S. Pat. No. 5,330,891) or proteins and carbohydrates (Warren et al., U.S. Pat. No. 5,328,825). Oligonucleotides attached to fluorescent particles are also described in Brinkley et al., U.S. Pat. No. 5,326,692. Oligonucleotide binding members having delimitative three dimensional configurations have also been employed, as in Lizardi et al., U.S. Pat. No. 5,312,728.

Clearly, there is a need for a simple, rapid system for producing activated surfaces capable of binding nucleic acid reagents in a loci specific manner. In this application we describe a chemical agent capable of producing an activated surface in only a single step. The activated surface is then capable of binding an unmodified nucleic acids without any additional process steps. Further, the availability of nucleic acid surfaces results in novel methodologies for using nucleic acids in diagnosis.

SUMMARY OF THE INVENTION

At present, nucleic acid analysis involves the separate steps of isolating nucleic acid; often followed by amplification by in vitro means such as polymerase chain reaction or in vivo plasmid cloning; followed by absorption of the target nucleic acid sequences to a filter; followed by hybridization of the target sequences to a probe sequence for analysis of label attached to a probe. "Label" in this case is a fluorophore, enzyme, binding agent such as biotin, radioisotope or chromophore. The presence of the label at the end of a series of steps implies the occurrence of a specific nucleotide sequence on the target.

The inventors have discovered a group of molecules with heterobifunctional crosslinking capabilities. When applied to nucleic acid immobilization these crosslinkers offer a means to provide loci specific covalent attachment without strand denaturation. Further, the invention provides for immobilization of a "capture" sequence that can hybridize and immobilize a target sequence in a sample. Thus, the inventors relieve the end user of the need to immobilize nucleic acids prior to assay. It is a further embodiment of the invention that a probe sequence, different from the capture sequence but also capable of hybridizing the target, can also be covalently bound to a plastic particle that has fluorescence, enzymatic or colorimetric properties. Thus, an assay using two plastic substrates is envisioned by the inventors such that detection of a target nucleic acid occurs as a result of the cooperation of immobilized capture and probe sequences. Such a system also allows the unexpected benefit of simultaneous amplification and detection of a nucleic acid, previously only possible by separate steps and apparatus. Simultaneous amplification and detection utilizes an area of the target nucleic acid sequence that is distinct from capture or probe sequences as an in vitro amplification primer site. When target nucleic acid, palmer, polymerase, nucleotide triphosphates, capture and probe are combined under conditions of thermal cycling only the target sequence will be amplified. Detection occurs when the copy number reaches a critical level for sufficient probe to become immobilized to capture nucleic acid through cooperative binding with target sequences. An added benefit is the ability to quantify the target nucleic acid when both the amount of starting nucleic acid is known and the number of cycles needed to obtain a positive signal.

The invention comprises a heterobifunctional molecule and plastic substrate to covalently mobilize nucleic acids. Substrates are articles of plastic and may be formed into beads, rods, cups, membranes, or tubes. Substrates may be of polymers of vinyl, ethylene, propylene, sulfone, carbonate, or a combination thereof. The heterobifunctional molecule comprises a molecule having three distinct regions. More specifically the molecule has a central ring structure and two functional groups at opposite positions. One functional region is a hydrocarbon "tail" or chain of three or more ethyl groups terminating in a methyl function. A second region joins at the ring position distal to the hydrocarbon tail and comprises one or more hydrophilic chains terminating in a reactive functional moiety. The reactive groups join the central ring at points that are hydrophilic in nature. This feature aids in the orientation of this molecule, highly hydrophobic on one end, wettable on the opposite end.

Reactive groups are those molecules that can react with a group on the nucleic acid polymer for immobilization. Reactive groups include, but are not limited to: hydroxy succinimide, nitrophenyl chloroformate, activated (reduced) thiol, trityl, tresyl chloride, acid halides, epoxides, diazo, or any other reactive group.

An important feature is the ability to produce nucleic acid coatings of importance in medical and environmental diagnostics.

Another important aspect of this invention is the ability to form an activated surface in a single step. After a brief (less than 5 minutes in most cases) contact with the activating molecule the surface is capable of binding reagent molecules.

BRIEF DESCRIPTION OF THE DRAWINGS

To illustrate the relationship between polynucleotide strands in some figures any pyrimidine nucleotide is abbreviated with a "Y" and any purine nucleotide is abbreviated as an "P".

DETAILED DESCRIPTION OF THE INVENTION

Figure 1A:
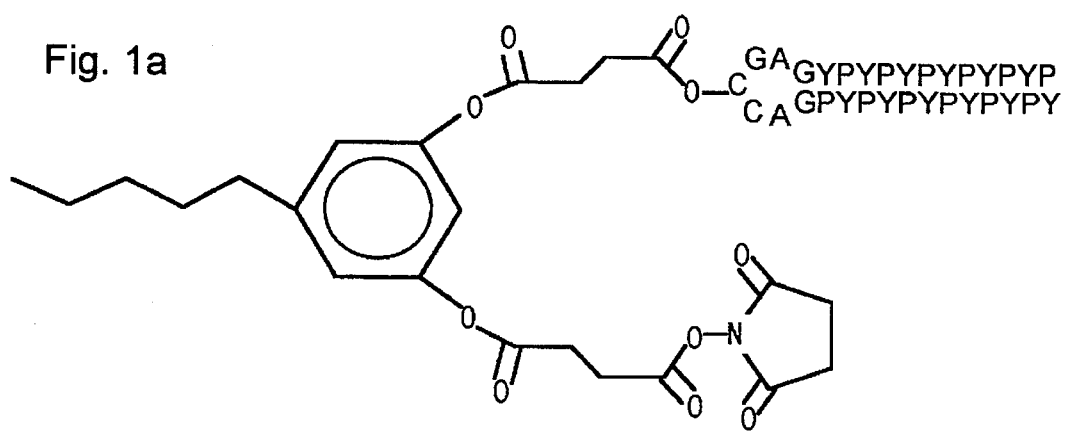
FIGS. 1a and 1b shows the orientation of polynucleotides reacted to the heterobifunctional crosslinker shown in FIG. 4 and described in the text.
Figure 1B:
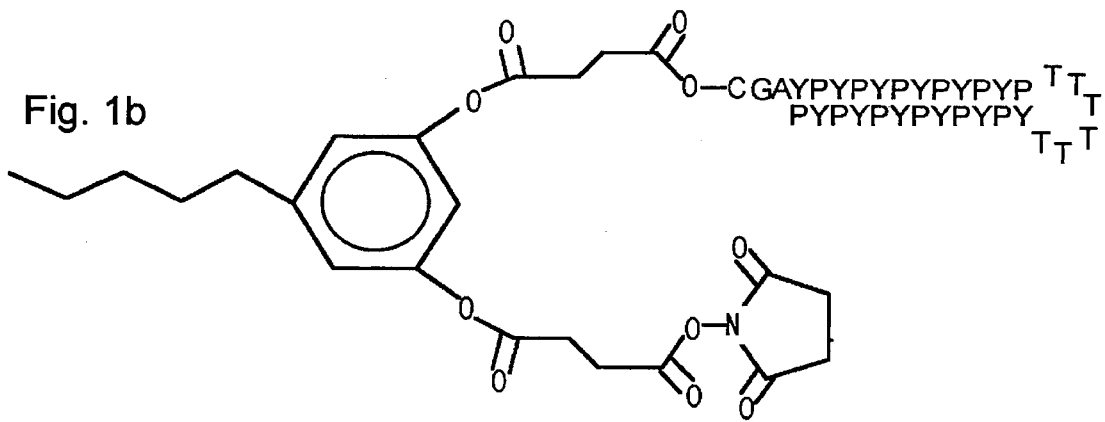

The invention for immobilizing nucleic acids comprises: a substrate; a heterobifunctional molecule having a hydrophobic tail attached to a central ring, and, in a separate structure on the ring opposite from the hydrophobic tall, a hydrophilic region with a reactive group; a "capture" probe nucleic acid sequence capable of both covalently attaching to the reactive group and also hybridizing with a "target" nucleic acid sequence of a sample; and a "detector" probe nucleic acid sequence capable of binding the immobilized target sequence.

In a preferred embodiment the hydrophobic tail of the heterobifunctional molecule comprises at least two ethyl groups terminating in a methyl group; the hydrophobic tail capable of intercalating the plastic substrate thereby anchoring the molecule and orientating the reactive moieties. In a preferred embodiment the second functional region comprises one or more hydrophilic chains terminating in a reactive functional moiety joined at the ring position distal to the hydrocarbon tail. In a further embodiment the point at which the reactive groups are bound to the ring is a hydrophilic bond such as an amine, hydroxyl, imine, hydroxylamine, carboxylic acid or other group. It is an embodiment of this invention that when an aqueous solution of reagent is applied the association of the hydrophobic region with the substrate is essentially irreversible and reactive groups extend into the solution to react with the reagent molecules.

A particularly unique embodiment of this invention is the ability of the heterobifunctional molecules described herein to form an activated surface in a single step. One need only contact the reagent to the plastic to have an activated surface capable of immobilizing a second reagent molecule. It is a particularly preferred embodiment that this activating step can be performed in only five minutes or less.

In a particularly preferred embodiment the heterobifunctional molecule is derived from reacting succinic anhydride to 5-pentyl resorcinol. The carboxylic acid groups thus obtained are then condensed with N-hydroxy-succinimide to produce reactive esters.

In a preferred embodiment the hydrophilic linkers on the central ring structure may be moieties derived from hydroxyls, amine or imines. In still another embodiment of this invention the linking groups between the hydrophilic ring moieties and the reagent binding groups may be from 1 to 6 carbons. In still another embodiment the reactive reagent binding groups may be N-hydroxy succinimide, sulfo-n-hydroxy succinimide or thionyl chloride.

The types of molecules that can be immobilized to the plastic by this molecule include, but are not limited to: enzymes; antibodies, both monoclonal and polyclonal; cellular proteins; nucleic acids, DNA, RNA and oligonucleotides; drugs; and xenobiotics.

Preferred substrates are plastics derived from polymers of acrylic, vinyl, ethylene, propylene, sulfone, carbonate, or a combination thereof. In a preferred embodiment the plastic substrate is a molded article, a coating, a pellicular or porous bead, or a porous sheet such as a membrane. In a particularly preferred embodiment the substrate is polystyrene formed in the shape of a microtiter well. In a particularly preferred embodiment the plastic article is a paddle-shaped "dipstick." In still another preferred embodiment the plastic substrate is a plastic bead of less than 1 mm diameter, the bead further having characteristics such as fluorescence; magnetic or paramagnetic properties; colored dyes; enzymatic activity, electro-, chemi-, or bioluminescence; or some other resolving property.

Reagent members comprise protein, nucleic acid, hapten or cell materials useful in assays. "Assays" in these embodiments comprise analysis of drugs, haptens, proteins, nucleic acids cells, or other molecules relevant to diagnosis. A full description of immunoassay methods and analytes are described in Tijssen, PRACTICE AND THEORY OF ENZYME IMMUNOASSAYS, LABORATORY TECHNIQUES IN BIOCHEMISTRY AND MOLECULAR BIOLOGY (1985), herein incorporated by reference. It is a particularly preferred embodiment that the assay be for nucleic acids of a specific sequence. Nucleic assay technology is described in Persing et al., DIAGNOSTIC MOLECULAR MICROBIOLOGY, PRINCIPLES AND APPLICATIONS, (1993), herein incorporated by reference.

It is particularly preferred embodiment that the reagent member bound to the reactive groups of the surface activating molecule is a nucleic acid. Nucleic acids in this instance implies either DNA or RNA, a synthetic nucleotide, or an artificial nucleic acid such as a peptide nucleic acids (PNA), and combinations thereof. The only requirement is that the nucleic acid polymer has a free nucleophile for binding to the reactive moiety. The free nucleophile may be provided by rendering DNA single stranded or by using a single strand of RNA wherein the amine groups of adenine, guanine, or cytosine occur without inter or intra strand hydrogen bonding. The free nucleophile may also be provided by modifications of DNA or RNA, either enzymatically by means such as polynucleotide kinase, or by the construction of oligomers through phosphodiester bonds common to nucleic acid synthesis.

It is a particularly preferred embodiment that the free nucleophile is provided as a short sequence of unpaired adenine, guanine, or cytosine (A, G, or C) wherein the short unpaired segment separates paired coding regions of DNA or RNA consisting of a first 5'-3' diagnostic coding sequence, followed by the short unpaired region of A, G, or C, followed by a second 5'-3' coding sequence that is an inverse complement of the first coding sequence; wherein the structure is of a "hairpin" consisting of a single polymer strand paired throughout much of its length; excepting the unpaired sequence of A, G, or C; said unpaired region of A, G, or C free to bind via the exposed amines of the bases to the heterobifunctional crosslinkers described herein, or other crosslinkers known to the art.

In still another embodiment of the invention a "hinge" joining loop of DNA or RNA is composed of thymine, or other base that lacks a free amine moiety, between the complementary paired coding regions of the polynucleotide. In this embodiment a short unpaired sequence of G, C, or A is appended to either the 3' or 5' end of the sequence to provide a "handle" for attachment of the polynucleotide to a substrate.

It is a particularly preferred embodiment that a capture nucleic acid sequence of the "hairpin" or "handle" type sequence described above be attached to a substrate, such as a dipstick, through the unpaired nucleophilic bearing bases by means of the heterobifunctional reagents herein described, or another means common to the art. It is also a preferred embodiment that a detector probe nucleic acid sequence of the "hairpin" or "handle" structure described above be attached to a plastic bead of less than 1 mm diameter; wherein the unpaired nucleophilic bearing residues are crosslinked to the bead by means of the heterobifunctional reagents herein described, or another means common to the art of nucleophile attachment; and the bead possesses properties such as fluorescence, luminescence, color, radioactivity or magnetism. Further that the capture nucleic acid coated dipstick and the detector nucleic acid coated beads work cooperatively to detect a target sequence of complementary polynucleotide. In still another embodiment both the capture and detector sequence have homology with a target sequence, but neither the capture or detector share any regions of homology with one another. In yet another embodiment of the system the capture and detector probe sequences lack a nucleic acid synthesis polymerase promoting sequence that occurs on the target sequence, wherein the target nucleic acid sequence may be selectively catalytically amplified in the presence of the capture and probe sequences without contamination with unbound capture and probe nucleic acid artifacts.

FIGS. 1a and b disclose the combination of a polynucleotide sequence reacted to a heterobifunctional immobilization reagent. To illustrate the relationship between the polynucleotide members that can bind the target polynucleotide, bases in the coding regions are shown with any pyrimidine nucleotide abbreviated as "Y" and a "P" used for any purine nucleotide. In the substrate binding members and "hinge" loops where the inventors intend to confine the structure to specific bases a "C", "G", "A", or "T" is used. This assay system provides anchoring for the polynucleotide without impairing the diagnostic sequences ability to hybridize. The heterobifunctional agent is that of FIG. 4, namely the compound SON. The diagnostic polynucleotide is meant to be representative of sequences in general, and not meant to be exclusionary in any way.

Figure 2:
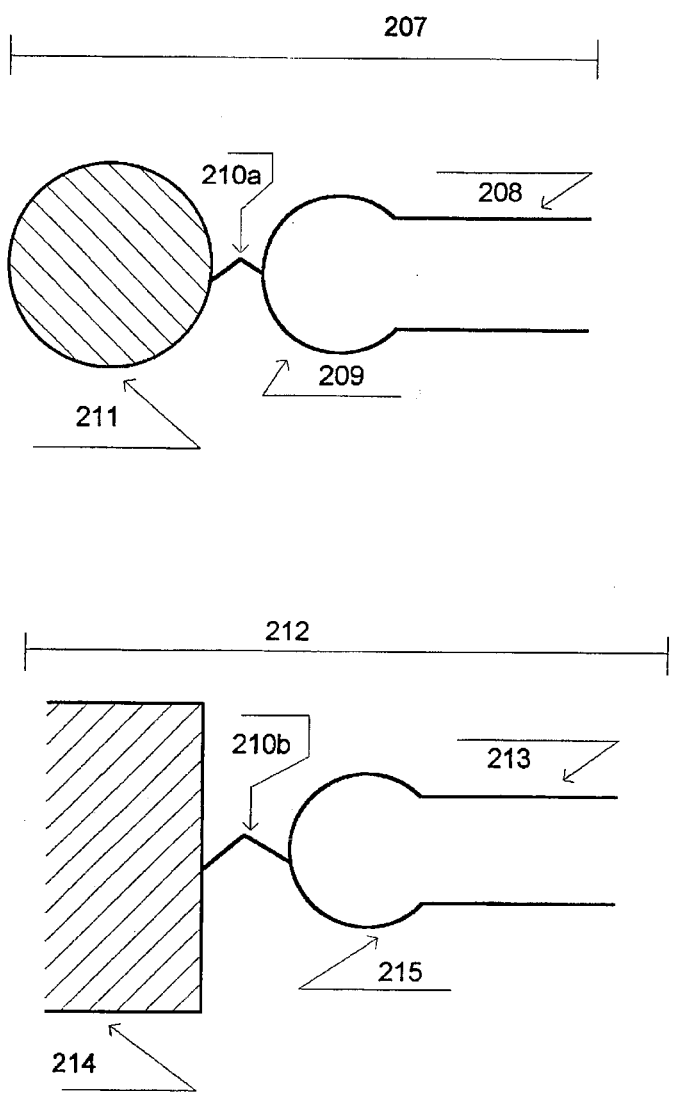
FIG. 2 is a schematic representation of the three polynucleotides described in the assay, and their relationship with the substrates as described in the text. The following elements are: 201, target polynucleotide member; 202a, target polynucleotide, (+) strand; 202b, target polynucleotide, (−) strand; 203, first in vitro amplification site; 204, second analytical binding site; 205, first analytical binding site; 206, second in vitro amplification site; 207, detector polynucleotide member; 208, detector analyte binding member; 209, detector substrate binding member; 210a, b, heterobifunctional crosslinker; 211, second substrate member; 212, capture polynucleotide member; 213, capture analyte binding member; 214, first substrate member; 215, capture substrate binding member.
Figure 2:
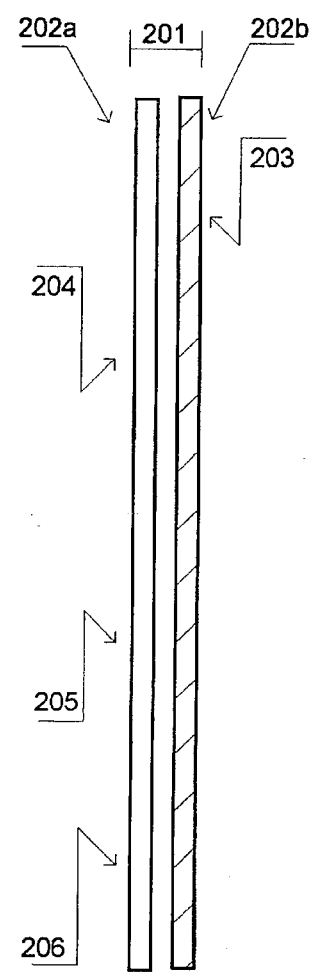

FIG. 2 discloses the inventors system for cooperatively detecting a target polynucleotide using capture and detector probes bound to substrates. The capture polynucleotide member (212) consists of a insoluble plastic substrate (214) with a single strand polynucleotide covalently bound by a heterobifunctional reagent member (210b). The attachment member is preferentially one of the heterobifunctional reagents described in the text. The attachment member is preferentially bound to free amines of guanine, cytosine or adenine occurring on a capture polynucleotide substrate binding member (215). The substrate binding member is formed when the two polynucleotide "arms" of the capture analyte binding member (213) form a double strand through intramolecular hydrogen binding of a complementary base sequence. The capture analyte binding member is capable of hybridizing with the first analytical binding site (205) of the target polynucleotide member (201). In essence, the single strand of the capture polynucleotide can hybridize with the complementary sequence of the double stranded target polynucleotide member by binding both the positive and negative strands (202 a,b). The target may also be single stranded leaving one-half of the capture analyte binding member unpaired. The detector polynucleotide member (207) is similarly formed by attachment of a single strand polynucleotide sequence to a plastic substrate (211) via a heterobifunctional reagent member (210a). Again, the detector substrate binding member (209) is formed through the interaction of the arms of the detector analyte binding member (208). The detector analyte binding member hybridizes the second analytical binding site (204) of the target polynucleotide member. In this manner the capture and detector sequences cooperatively detect a target polynucleotide. For the convenience of the enduser in vitro amplification sites may be incorporated into the system (203,206).

Figure 3:
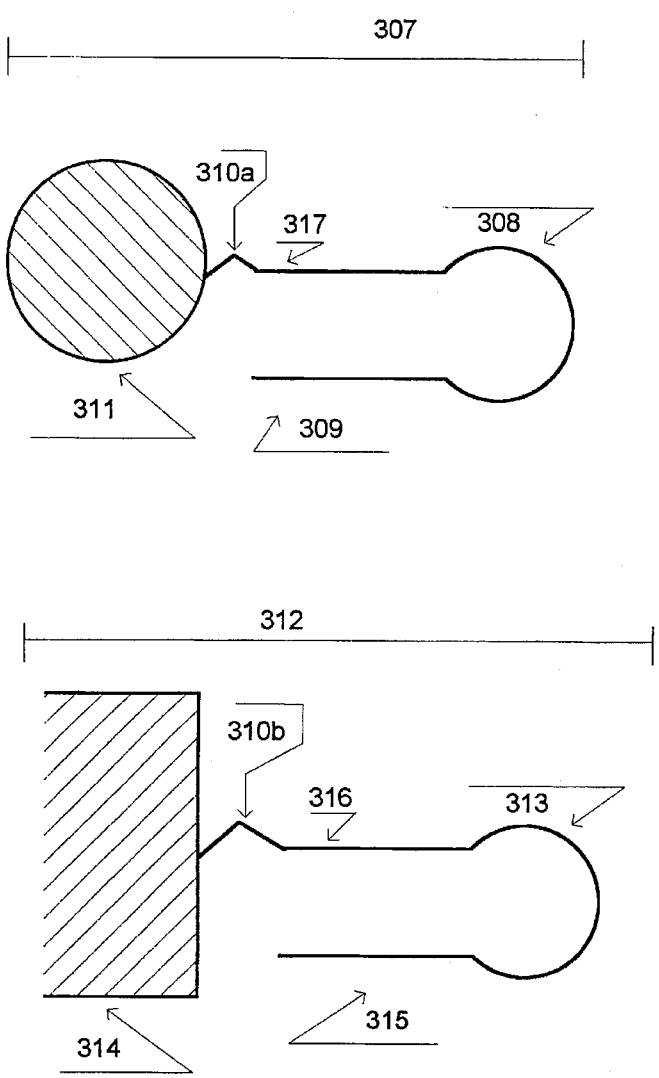
FIG. 3 is a schematic representation showing an alternate orientation of the three polynucleotides described in the assay, and their relationship with the substrates as described in the text. The following elements are: 301, target polynucleotide member; 302a, target polynucleotide, (+) strand; 302b, target polynucleotide, (−) strand; 303, first in vitro amplification site; 304, second analytical binding site; 305, first analytical binding site; 306, second in vitro amplification site; 307, detector polynucleotide member; 308, detector hinge member; 309, detector analyte binding member; 317, detector substrate binding member; 310a, b, heterobifunctional crosslinker; 311, second substrate member; 312, capture polynucleotide member; 313, capture hinge member; 315, capture analyte binding member; 314, first substrate member; 316, capture substrate binding member.
Figure 3:
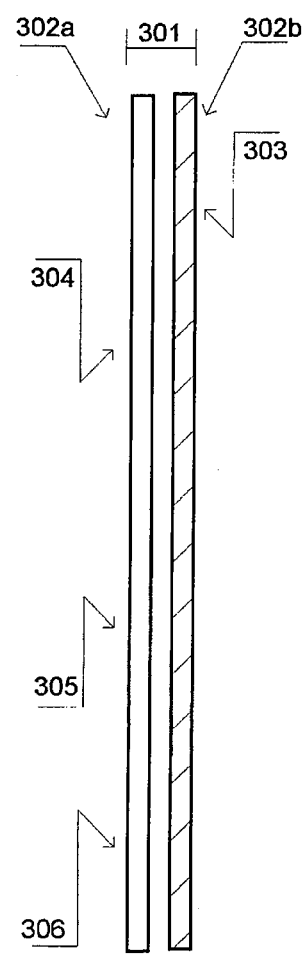

FIG. 3 discloses an alternate method for forming the hybridizable "arms" of the inventors detection system. In this instance the inventors provide the substrate binding members (316 and 317) as an appendage attached to either the 3' or 5' terminus of the capture or detector polynucleotide. A short sequence of either thymine, uracil, or other base lacking a free amino terminus is placed between the complementary analyte binding members (308 or 3 13). Thus, the only free amines for crosslinking are in the "handle" region, not on the loop as previously described. The capture polynucleotide member (312) consists of a insoluble plastic substrate (314) with a single strand polynucleotide covalently bound by a heterobifunctional reagent member (310b). The attachment member is preferentially one of the heterobifunctional reagents described in the text. The heterobifunctional reagent member is preferentially bound to free amines of guanine, cytosine or adenine occurring on a capture polynucleotide substrate binding member (316). The substrate binding member is formed when the two polynucleotide "arms" of the capture analyte binding member (315) form a double strand through intramolecular hydrogen binding of a complementary base sequence. The capture analyte binding member is capable of hybridizing with the first analytical binding site (305) of the target polynucleotide member (301). In essence, the single strand of the capture polynucleotide can hybridize with the complementary sequence of the double stranded target polynucleotide member by binding both the positive and negative strands (302 a,b). The target may also be single stranded leaving one-half of the capture analyte binding member unpaired. The detector polynucleotide member is similarly formed by attachment of a single strand polynucleotide sequence to a plastic substrate (311) via a heterobifunctional reagent member (310a). Again, the detector substrate binding member (317) is formed through the interaction of the arms of the detector analyte binding member (309). The detector analyte binding member (309) hybridizes the second analytical binding site (304) of the target polynucleotide member. In this manner the capture and detector sequences cooperatively detect a target polynucleotide. For the convenience of the enduser in vitro amplification sites may be incorporated into the system (303, 306).

The inventors envision the first substrate member as being either a dipstick, cell, or well. Further, the second substrate member is most likely to be utilized as a small (less than 1 mm) bead with colorimetric, fluorescent, or other properties for ease in detection. It is an important consideration in this invention that polynucleotide immobilization with the heterobifunctional crosslinker provides a nucleotide sequence that is free to form interstrand hybridizations with its complement.

This disclosure will enable those skilled in the art to grasp the potential of these novel heterobifunctional agents to produce immobilized nucleic assay devices. Examples herein described are meant to be illustrative only and not limitive on the scope of the invention.

The following reagents were used in the course of developing this invention. Sources are given where relevant, otherwise they are of the standard commercial grades available.

Phosphate Buffered Saline (PBS): 0.1M, pH 7.2. Available from Sigma Chemical, St. Louis Mo.

PBS-Tween: PBS solution with 0.1% tween detergent.

Saline sodium citrate (SSC): 0.05M Solution. Available from Sigma Chemical, St. Louis Mo.

Non-specific blocking solution (NSB Solution): Denhardt's solution, available from Sigma Chemical, St. Louis Mo. Diluted in SSC.

Biotinylated lambda DNA cut with Hind III restriction endonuclease. Available from Sigma Chemical, St. Louis Mo.

Biotinylated lambda DNA cut with Hind III, single strand. Labeled lambda fragments diluted in SSC, heated to 80° C. and quickly cooled.

Lambda DNA, whole genome and cut with Hind III restriction endonuclease. Available from Sigma Chemical, St. Louis Mo.

Herpes DNA, synthesized for the inventors by National Biosciences Inc. (Plymouth, Minn.).

Lambda DNA, single strand. Lambda DNA diluted in SSC, heated to 80° C. and quickly cooled.

Extravidin™ conjugated to horseradish peroxidase enzyme solution: Available from Sigma Chemical, St. Louis Mo., diluted in SSC solution.

Enzyme Substrate: Tetramethyl benzidine (TMB) solution was obtained from Kirkegaard and Perry, Gaithersberg, Md.

EXAMPLE 1

Figure 4:
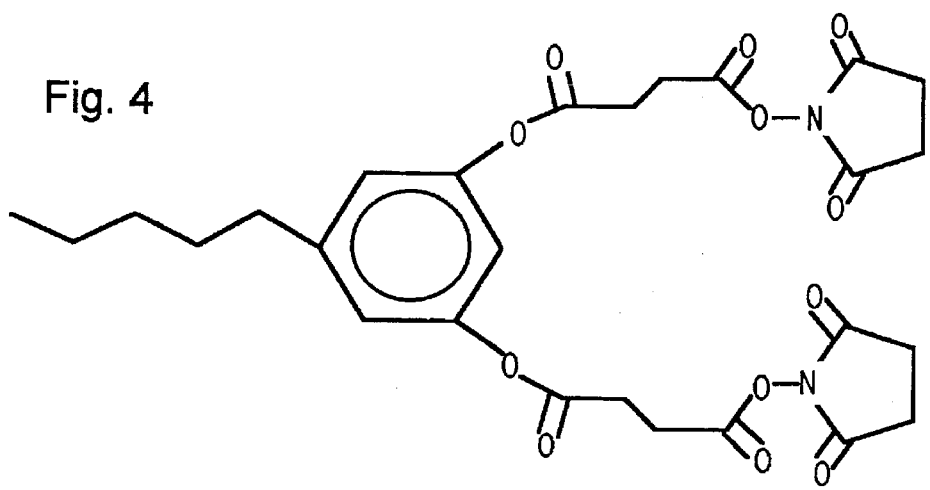
FIG. 4 shows the structure of the heterobifunctional crosslinker developed using dioximino pentyl benzene as a starting material.
Figure 5:
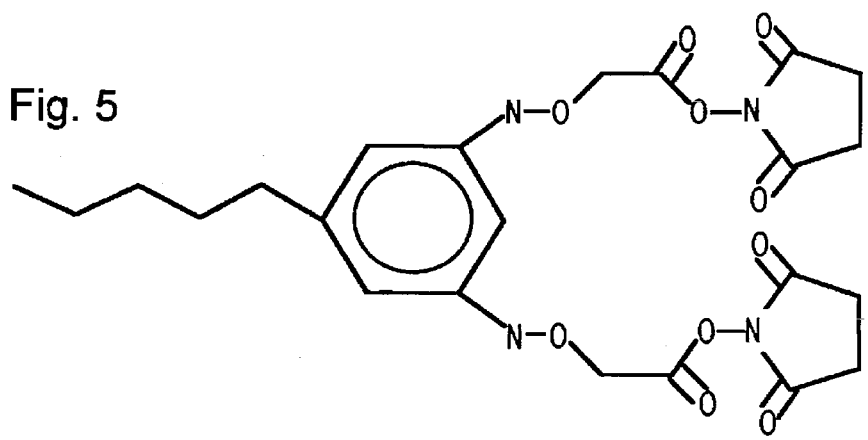
FIG. 5 shows the structure of the heterobifunctional crosslinker developed using dihydroxy pentyl benzene as a starting material.
Figure 6:
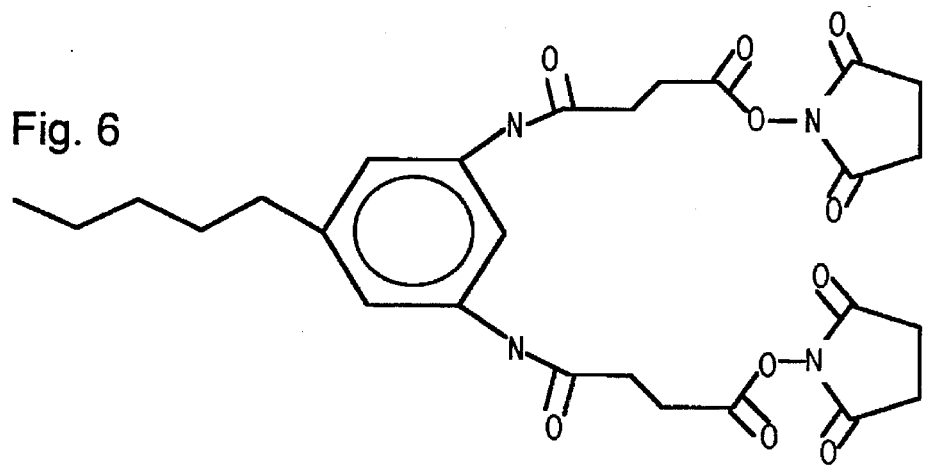
FIG. 6 shows the structure of the heterobifunctional crosslinker developed using diamino pentyl benzene as a starting material.

Synthesis of succinyl-olivetol-N-hydroxy succinimide (SON) compound shown in FIG. 4 was accomplished as follows. All materials and solvents were obtained from Aldrich Chemicals (Milwaukee, Wis..). 0.1 g of pentyl resorcinol was dissolved in 2 mls dioxane. In a separate container anhydrous succinic arthydride in excess of two moles w/w was dissolved in two mls dioxane. Both solutions were added to a sealed glass vessel under nitrogen and sonicated for 60 minutes in a 45 watt sonicating bath, followed by 6 hours at 60 degrees centigrade. The solvent was removed under a nitrogen stream and the brown oil thus obtained was resuspended in dichloromethane. The solution was washed with two volumes of water, and the organic phase was dried with molecular sieve and the solvent removed under a nitrogen stream. The oil was resuspended in dioxane and N-hydroxy-succinimide equivalent to two moles w/w were added. The final compound was obtained by adding the condensing agent dicyclocarbodiimide. The crystals of dicyclourea were removed by filtration and the resulting SON purified by standard chromatographic means. The usefulness of this compound is demonstrated by the following examples.

EXAMPLE 2

Succinyl-olivetol-N-hydroxy succinimide prepared as describe in Example 1 is used to produce plastic beads. SON dissolved to a concentration of 2 mg/ml in methanol and added to a 0.1 gram of polyethylvinyl acetate beads, 1 micron average diameter (Polysciences, Warrington, Pa.). After evaporation of the solvent under a nitrogen stream the beads are capable of immobilizing nucleic acids.

EXAMPLE 3

Using pentyl resorcinol as a starting material a second derivative is made. Pentyl resorcinol is dissolved in dioxane. Two moles of glutaric anhydride are added and reacted at temperatures and conditions sufficient to produce the ester. The free carboxylic acid groups on glutarate are converted to the corresponding acid chlorides through the action of thionyl chloride. The reagent thus obtained has the ability to crosslink amines, imines, and hydroxylated compounds to plastic surfaces under both aqueous and organic conditions.

EXAMPLE 4

An additional heterobifunctional reagent was synthesized starting with Olivetol treated with an excess of potassium permanganate oxidizer to yield dicarbonyl pentyl benzene. This compound was further reacted with Hydroxylamine to produce an oxime. Subsequent reduction with hydrogen in the presence of palladium catalyst yielded diamino pentyl benzene. The free amines thus obtained were reacted with an excess of succinic anhydride. Esterification with N-hydroxy-succinimide yielded the heterobifunctional agent.

EXAMPLE 5

The carbonyl oxygens of dicarbonyl pentyl benzene were reacted with carbomethoxyamine to produce a dioxime. The carboxylic acid moieties were subsequently esterified with N-hydroxy-succinimide to produce the heterobifunctional agent.

EXAMPLE 6

Binding of Biotinylated DNA to dipsticks coated with SON.

In this example the plastic surface is a paddle-like "dip-stick" having a wide flat reaction area (about 5 mm by 10 mm) connected by a stem of material forming a handle. The dipstick is composed of molded polystyrene. The use of a dipstick allows the rapid derivatizing aspect of the invention to be more fully illustrated.

Polystyrene dipsticks were coated with SON, prepared as in example 1, diluted to 4 mg/ml in methanol or were blanks dipped in methanol without SON. The dipsticks were dried free of solvent and placed in a solution of SSC containing 2 ng/ml of Hind III digested lambda genome labeled with biotin, either single or double stranded. After 20 minutes the dipsticks were rinsed briefly in PBS-tween and immersed in a solution of extravidin-peroxidase (1:2000 dilution). After 20 minutes at room temperature the dipsticks were removed and briefly rinsed. The amount of enzyme binding was determined by addition of TMB enzyme substrate. SON greatly increased binding of DNA on polystyrene dipsticks, further, clear differences could be seen between the amount of label present in single versus double strand DNA (Table 1).

TABLE 1

| Comparisons of Single and Double Strand DNA Attachment with and without SON. | | |
|---|---|---|
| SON DS | SON SS | Blank |
| 0.534 | 0.169 | 0.01 |

EXAMPLE 7

Two SON Activated dipsticks prepared as in Example 6 were treated with double stranded biotinylated Hind III digested lambda DNA. One was heated in 5XSSC to 80° C. for 30 minutes. The second was left at room temperature in 5XSSC. Both were then reacted with Extravidin™ peroxidase and tested for enzyme binding. Heating to melting temperature resulted in reduction of signal by one-half, consistent with that observed for single strand DNA observed in Table 1. These data show the stability of the derivatized surface and demonstrates the covalent nature of the bond.

EXAMPLE 8

Detection of Herpes DNA Hybridization with an activated dipstick

Two probes capable of hybridizing different areas of the Herpes DNA polymerase gene were generated. The two diagnostically significant sequences were located about 0.5 kilobases apart.

Sequence A was:
5'-GCTGACCAGCACCACCTGGTCAGCTTT-3'
Sequence B was:
5"-TTTATCAACCGCGCACCAACCACGGTGCGGTT GAT-3'

The sequences each carry an short region hybridizable to the Herpes polymerase gene as well as self-hybridizing into a hairpin loop. This hairpin structure results in an unhybridizing region of amine-beating nucleotides that are not part of the Herpes polymerase gene. The result is a portion of the Herpes gene that can be immobilized via amines on the unhybridized nucleotides.

EXAMPLE 9

Sequence A of Example 8 was reacted to the paddles of Example 6 to form a DNA coated surface. Sequence B of Example 8 was reacted to activated fluorescent beads produced by washing fluorescent latex beads "Fluoresbrite" 0.5 micron, Polysciences Inc., Warrington, Pa.) with methanol and then reacting the dried beads with SON of Example 1.

In a test of the system the DNA coated dipsticks were immersed into a solution of DNA coated fluorescent beads in a hybridization buffer of 5X Saline Sodium Gitrate (Sigma Chemicals). Herpes DNA was added to the hybridization mixture at amounts from 0 to 1,000 picograms. The test mixtures were heated to a denaturation temperature of over 90 degree C. and then allowed to reanneal at a temperature of between 75–80 degrees C.

The results were scored by two different methods: 1) visually under fluorescent blacklight with the results given in Table 2; and, 2) using video micrography with particle counting software (Table 3).

TABLE 2

Visual Scoring of Hybridization.

| | |
|---|---|
| 0 picograms | negative |
| 50 picograms | weak positive |
| 100 picograms | weak/moderate |
| 500 picograms | strong positive |
| 1000 picograms | strong positive |

TABLE 3

Particle counting of hybridization using video micrography. For this study an Olympus B-Max 60 trinocular microscope outfitted with epifluorescent illumination and a Sony Hi-Resolution Color Video Camera interfaced with an automatic Image Analyzer Board (DIAS-1b) from C-Squared Corporation (Olympus Optical Corporation).

| Amount of Herpes DNA per Assay | Beads per $mm^2$ | Estimated number of hybridized beads |
|---|---|---|
| 0 Negative control | 69 | 0 |
| 1 ng DNA | 94 | 525 |
| 10 ng DNA | 358 | 10,115 |

We claim:

1. An assay preparation containing a capture polynucleotide covalently bound to a first substrate and a detector polynucleotide covalently bound to a second substrate, said preparation produced by the method comprising the steps of:
   a) contacting the surface of a first substrate member with a heterobifunctional crosslinking agent to produce a first activated surface; and, contacting said first activated surface on said first substrate member with a capture polynucleotide member; wherein, said capture polynucleotide member reacts covalently with said first activated surface and becomes covalently bound thereto; and,
   b) contacting the surface of a second substrate member with said heterobifunctional crosslinking agent to produce a second activated surface; and, contacting said second activated surface on said second substrate member with a detector polynucleotide member; wherein, said detector polynucleotide member reacts covalently with said second activated surface and becomes covalently bound thereto; said second substrate member further has a fluorescent, colorimetric, magnetic or radioactive detection means;

wherein said capture polynucleotide member and said detector polynucleotide member are individually hybridizable with said target polynucleotide to immobilize and detect said target polynucleotide; and, wherein said heterobifunctional crosslinking agent for producing said activated surfaces has the structure:

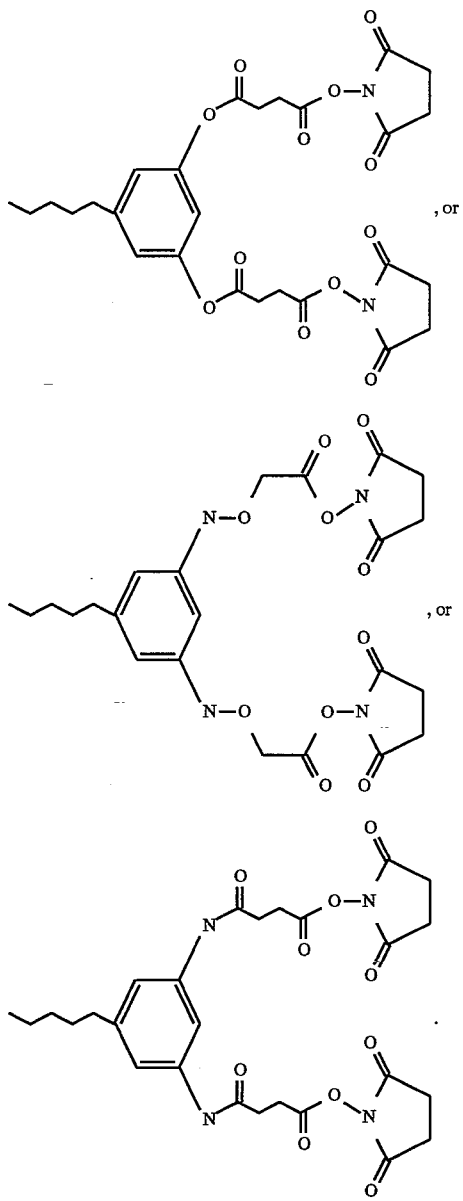

2. The preparation of claim 1 wherein said first substrate member is comprised of a plastic substrate made from a polymer selected from the group consisting of polypropylene, polyethylene, polycarbonate, polysulfone, polyvinyl, polymethacrylate, and derivatives and combinations thereof; said plastic being in the form of a sheet, cup, rod, tube, fiber, or coating, either porous or non-porous.

3. The preparation of claim 1 wherein said second substrate member is comprised of a plastic substrate of less than 1 mm diameter made from a polymer selected from the group consisting of polypropylene, polyethylene, polycarbonate, polysulfone, polyvinyl, polymethacrylate, and derivatives and combinations thereof; said plastic being in the form of particles either porous or non-porous.

4. The preparation of claim 1, wherein said capture polynucleotide member further comprises:

a) a single strand polynucleotide having a 5' end and a 3' end, said single strand polynucleotide having first and second capture polynucleotide analyte binding members, said single strand polynucleotide further having a capture polynucleotide substrate binding member; wherein, b) said first capture polynucleotide analyte binding member is a 5' to 3' polynucleotide capable of hybridizing a first analyte member of said target polynucleotide; and, c) said first capture polynucleotide analyte binding member is followed by said capture polynucleotide substrate binding member of between 4 and 12 randomly ordered nucleotides of either, guanine, cytosine or adenine; and, d) said capture polynucleotide substrate binding member is followed by said second capture polynucleotide analyte binding member; wherein, e) said first and second capture polynucleotide analyte binding members hybridize forming a double strand through intrastrand pairing, said capture polynucleotide substrate binding member remains as a single strand unpaired loop; wherein, f) said single strand unpaired loop of said capture polynucleotide substrate binding member is covalently immobilized to said first activated surface on said first substrate member; and, g) said immobilized capture polynucleotide member is capable of hybridizing with said first analyte member of said target polynucleotide by interstrand pairing to immobilize said target polynucleotide.

5. The preparation of claim 1, wherein said detector polynucleotide member further comprises:

a) a single strand polynucleotide having a 5' end and a 3' end, said single strand polynucleotide having first and second detector polynucleotide analyte binding members, said single strand polynucleotide further having a detector polynucleotide substrate binding member; wherein, b) said first detector polynucleotide analyte binding member is a 5' to 3' polynucleotide capable of hybridizing a second analyte member of said target polynucleotide; and, c) said first detector polynucleotide analyte binding member is followed by said detector polynucleotide substrate binding member of between 4 and 12 randomly ordered nucleotides of either, guanine, cytosine or adenine; and, d) said detector polynucleotide substrate binding member is followed by said second detector polynucleotide analyte binding member; wherein, e) said first and second detector polynucleotide analyte binding members hybridize forming a double strand through intrastrand pairing, said detector polynucleotide substrate binding member remains as a single strand unpaired loop; wherein, f) said single strand unpaired loop of said detector polynucleotide substrate binding member is covalently immobilized to said second activated surface on said second substrate member; and, g) the immobilized detector polynucleotide member is capable of hybridizing with said second analyte member of said target polynucleotide by interstrand pairing to immobilize said target polynucleotide.

6. The preparation of claim 1, wherein said capture polynucleotide member further comprises:

a) a single strand polynucleotide having a 5' end and a 3' end, said single strand polynucleotide having first and second binding members, said single strand polynucleotide further having a hinge member and a capture polynucleotide substrate binding member; wherein, b) said first binding member is a 5' to 3' polynucleotide capable of hybridizing said first analyte member of said target polynucleotide; and, c) said first binding member is followed by said hinge member of 4 to 12 thymines or uracils; and, d) said hinge member is followed by said second binding member containing a 5' to 3' polynucleotide with a base sequence that has a nucleotide sequence complementary to said first binding member; and, e) said capture polynucleotide substrate binding member of between 4 and 12 randomly ordered nucleotides of either, guanine, cytosine or adenine is provided attached to either the 5' end of said first binding member or the 3' end of said second binding region; wherein, f) said first binding member of said capture polynucleotide member hybridizes with said second binding member of said capture polynucleotide forming a double strand through intrastrand pairing, said hinge member thereby remaining as a single strand unpaired loop; and, g) said capture polynucleotide substrate binding member is unpaired and covalently immobilized to said first activated surface on said first substrate member by the amine groups of said capture polynucleotide substrate binding; and, h) said capture polynucleotide member is capable of hybridizing with said first analyte member of said target polynucleotide by interstrand pairing with said first and second binding members to immobilize said target polynucleotide.

7. The preparation of claim 1, wherein said detector polynucleotide member further comprises:

a) a single strand polynucleotide having a 5' end and a 3' end, said single strand polynucleotide having first and second binding members, said single strand polynucleotide further having a hinge member and a detector polynucleotide substrate binding member; wherein, b) said first binding member is a 5' to 3' polynucleotide capable of hybridizing said second analyte member of said target polynucleotide; and, c) said first binding member is followed by said hinge member of 4 to 12 thymines or uracils; and, d) said hinge member is followed by said second binding member containing a 5' to 3' polynucleotide with a base sequence that has a nucleotide sequence complementary to said first binding member; and, e) said detector polynucleotide substrate binding member of between 4 and 12 randomly ordered nucleotides of either, guanine, cytosine or adenine is provided attached to either the 5' end of said first binding member or the 3' end of said second binding region; wherein, f) said first binding member of said capture polynucleotide member hybridizes with said second binding member of said capture polynucleotide forming a double strand through intrastrand pairing, said hinge member thereby remaining as a single strand unpaired loop; and, g) said detector polynucleotide substrate binding member is unpaired and covalently immobilized to said second activated surface on said second substrate member by the amine groups of said detector polynucleotide substrate binding member; and, h) said detector polynucleotide member is capable of hybridizing with said second analyte member of said target polynucleotide by interstrand pairing with said first and second binding members to immobilize said target polynucleotide.

* * * * *